United States Patent
Hwu et al.

(10) Patent No.: US 11,714,031 B2
(45) Date of Patent: Aug. 1, 2023

(54) METHOD FOR VISUALIZING NEURONS

(71) Applicant: Yeu-Kuang Hwu, New Taipei (TW)

(72) Inventors: Yeu-Kuang Hwu, New Taipei (TW);
Shin-Tai Chen, Taipei (TW);
Shun-Min Yang, Taipei (TW)

(73) Assignee: Yeu-Kuang Hwu, New Taipei (TW)

( * ) Notice: Subject to any disclaimer, the term of this patent is extended or adjusted under 35 U.S.C. 154(b) by 558 days.

(21) Appl. No.: 16/881,932

(22) Filed: May 22, 2020

(65) Prior Publication Data

US 2020/0284705 A1    Sep. 10, 2020

Related U.S. Application Data

(63) Continuation-in-part of application No. 15/954,093, filed on Apr. 16, 2018, now abandoned.

(30) Foreign Application Priority Data

Apr. 21, 2017 (TW) .................................. 106113526

(51) Int. Cl.
*G01N 1/30* (2006.01)
*G01N 1/36* (2006.01)

(52) U.S. Cl.
CPC ................. *G01N 1/30* (2013.01); *G01N 1/36* (2013.01); *G01N 2001/302* (2013.01); *G01N 2001/305* (2013.01); *G01N 2001/364* (2013.01)

(58) Field of Classification Search
None
See application file for complete search history.

(56) References Cited

PUBLICATIONS

Ranjan et al. "A modified method for consistent and reliable Golgi-Cox staining in significantly reduced time." Frontiers in Neurology 1 (2010): 157. (Year: 2010).*
Narayanan et al. "Determining factors for optimal neuronal and glial Golgi-Cox staining." Histochemistry and Cell Biology 154.4 (2020): 431-448. (Year: 2020).*
Das et al. "The Golgi-Cox Method." Neural Development. Humana Press, Totowa, NJ, 2013. 313-321. (Year: 2013).*
Spurr "A low-viscosity epoxy resin embedding medium for electron microscopy," Journal of Ultrastructure Research, 1969, pp. 31-43, vol. 26, Academic Press Inc.
Robbin Gibb et al., "A method for vibratome sectioning of Golgi-Cox stained whole rat brain", Journal of Neuroscience Methods, Jan. 31, 1998, pp. 1-4, vol. 79(1).
Moss et al. "Techniques for thick-section Golgi impregnation of formalin-fixed brain tissue." Trinucleotide Repeat Protocols, Methods for Molecular Biology, Humana Press, 2004, pp. 277-285, vol. 277.
Anan Li et al., "Micro-optical sectioning tomography to obtain a high-resolution atlas of the mouse brain", Science, Nov. 4, 2010, pp. 1-13, 1191776.
Anan Li et al., "Micro-optical sectioning tomography to obtain a high-resolution atlas of the mouse brain", Science, Dec. 3, 2010, pp. 1404-1408, vol. 330.
Chung Jr et al., "Multiscale exploration of mouse brain microstructures using the knife-edge scanning microscope brain atlas", Frontiers in Neuroinformatics, Nov. 22, 2011, pp. 1-17, vol. 5:29.
Levine ND et al., "Advances in thin tissue Golgi-Cox impregnation: fast, reliable methods for multi-assay analyses in rodent and non-human primate brain", Journal of Neuroscience Methods, Mar. 15, 2013, pp. 214-227, vol. 213(2).
Mizutani et al. "X-ray microtomography in biology." Micron, (2012): pp. 104-115, vol. 43.2-3.
Bayram-Weston et al. "Optimising Golgi-Cox staining for use with perfusion-fixed brain tissue validated in the zQ175 mouse model of Huntington's disease." Journal of Neuroscience Methods, (2016), pp. 81-88, vol. 265.
Zaqote et al., "Golgi-Cox staining step by step", Front Neuroanat, 2016, pp. 1-7, vol. 10, Article 38.

* cited by examiner

*Primary Examiner* — Emily A Cordas
(74) *Attorney, Agent, or Firm* — Muncy, Geissler, Olds & Lowe, P.C.

(57) ABSTRACT

A method for visualizing neurons is provided. The method comprises a staining step and a visualizing step. The staining step comprises following steps: placing a neural tissue sample in an acrolein solution in the dark for fixation; placing the fixed neural tissue sample in a Golgi-Cox solution in the dark; replacing the Golgi-Cox solution; incubating the neural tissue sample placed in the replaced Golgi-Cox solution at a range of 36° C. to 38° C.; gradiently dehydrating the neural tissue sample; and embedding the dehydrated neural tissue sample with Petropoxy 154 resin. The visualizing step comprises: performing data acquisition and image reconstruction on the neural tissue sample using X-ray microscopy.

17 Claims, 8 Drawing Sheets

METHOD FOR VISUALIZING NEURONS

CROSS REFERENCE TO RELATED APPLICATIONS

This application is a Continuation-In-Part (CIP) of U.S. Ser. No. 15/954,093 filed on Apr. 16, 2018, which claims priority under 35 U.S.C. § 119(a) on Patent Application No(s). 106113526 filed in Taiwan, Republic of China on Apr. 21, 2017, the entire contents of which are hereby incorporated by reference.

BACKGROUND OF THE INVENTION

Field of Invention

The present disclosure relates to a method and kit for staining a neural tissue sample, which may use with X-ray microscopy for visualizing neurons.

Related Art

Golgi-Cox staining is a method for staining neurons and discovered by Camillo Golgi in 1873. This method is to stain neurons by placing the neural tissue in the potassium dichromate solution and the silver nitrate solution. However, it requires the neural tissue to be immersed in the aforementioned solutions for a long time. The conventional Golgi-Cox staining is characterized in that the neurons in the neural tissue is stained with a hit rate of 1%-3% (Zaqout et al, (2016). Golgi-Cox staining step by step. Front Neuroanat. 2016; 10: 38), such that the neurological morphology of the neural tissue can be seen.

Figure 1:
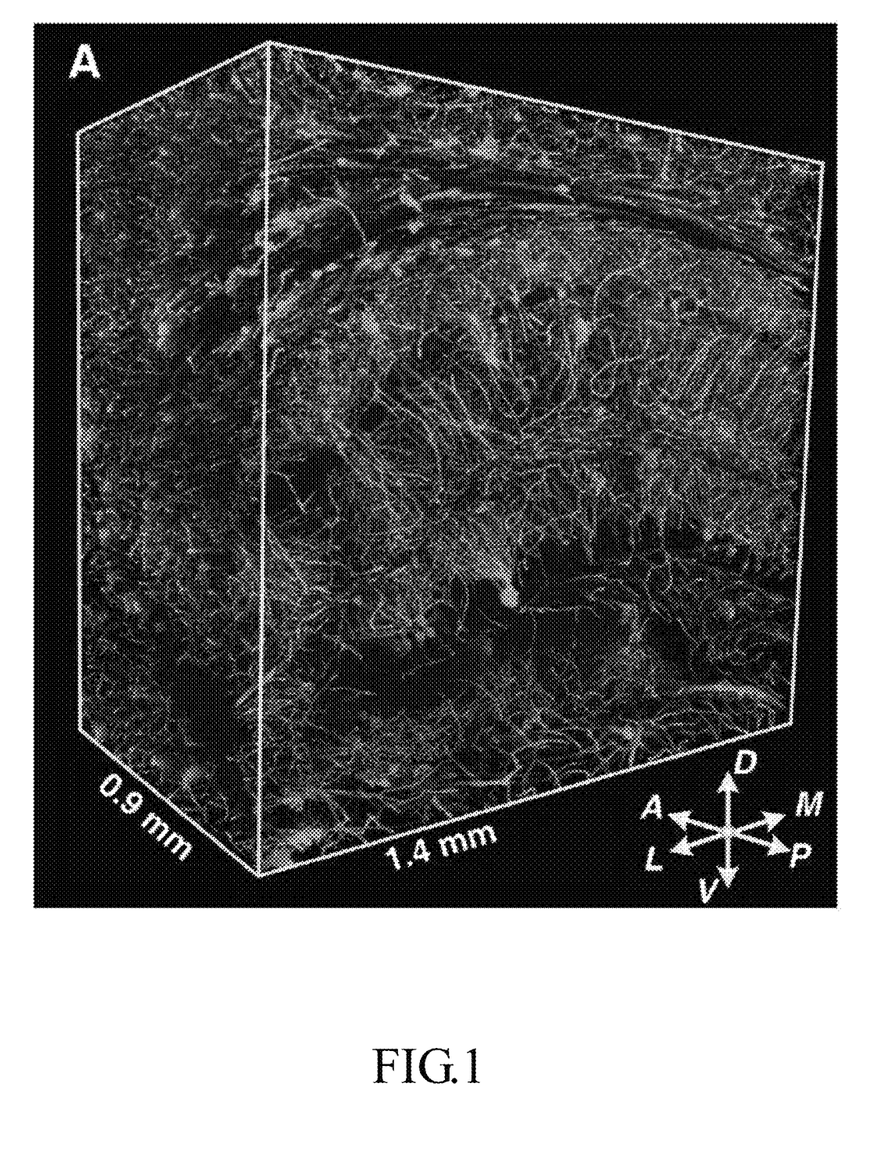
FIG. 1 is an image depicting a large volumetric reconstruction of a partial hippocampus of the mouse brain acquired through MOST.

Several studies have been made to modify the conventional Golgi-Cox staining method, with a limited hit rate. As shown in the study made by Anan Li et al. (Anan Li et al. (2010). Micro-optical sectioning tomography to obtain a high-resolution atlas of the mouse brain. Science, 330, 1404-8), a whole mouse brain sample is prepared and stained by the modified Golgi-Cox staining method and embedded with Spurr resin. Later, the image data are acquired by the Micro-Optical Sectioning Tomography (MOST) system which is developed by the authors. Throughout data acquisition, the section thickness was 1.0 µm, and an objective (40×, numerical aperture 0.8) was used for imaging. Please refer to FIG. 1, which is an image depicting a large volumetric reconstruction of a partial hippocampus of the mouse brain acquired through the aforementioned method. However, in the process developed by Anan Li et al., the whole mouse brain has to be immersed in the Golgi-Cox solution for 180 days. In other modification, such as the study of JR Chung et al. (JR Chung et al. (2010). Multiscale exploration of mouse brain microstructures using the knife-edge scanning microscope brain atlas. Front Neuroinform, 5, doi:10.3389/fninf.2011. 00029), the mouse brain has to be immersed in the Golgi-Cox solution for 10-16 weeks. These modifications requires the tissues or organs to be placed in the staining solutions for a long time, which may result in tissue deformation.

In addition to the long-term staining, the existing Golgi-Cox staining methods may have difficulty to present a reconstructed 3D image which has an actual neuroanatomical connectivity of the nerve system because of their low hit rates (1%-3%). In detailed, as discussed as above, because only 1% to 3% of neurons are stained by the existing Golgi-Cox staining methods, when a certain neuron is shown to be not connected with other neurons, it is not sure that there are actually no such neurons that are connected with it. Or, there are such neurons, but they are just not shown because of not being stained. Hence, even with a high-resolution 3D imaging system, a precise neuroanatomical connectivity is still unavailable when a conventional Golgi-Cox staining method is used.

Hence, it has become an urgent need to provide a method and kit for staining a neural tissue sample, without long-term staining but with an elevated hit rate, to be able to observe the detailed morphology of the neural tissue under a high-resolution X-ray microscope.

SUMMARY OF THE INVENTION

According to an objective of the present disclosure, a method and kit for staining neural tissue sample with an elevated hit rate but without long-term staining are provided. This method and kit can be used with the high-resolution X-ray microscopy to observe the detailed neural morphology and the neuroanatomical connectivity of the neural tissue sample.

The present disclosure provides a method for visualizing neurons. The method comprises a staining step and a visualizing step. The staining step comprises the following steps: placing a neural tissue sample in an acrolein solution in the dark for fixation; placing the fixed neural tissue sample in a Golgi-Cox solution in the dark; replacing the Golgi-Cox solution; incubating the neural tissue sample placed in the replaced Golgi-Cox solution at a temperature ranging from 36° C. to 38° C.; gradiently dehydrating the neural tissue sample; and embedding the dehydrated neural tissue sample with Petropoxy 154 resin. The visualizing step comprises the following step: performing data acquisition and image reconstruction on the neural tissue sample using X-ray microscopy.

In one embodiment, the neural tissue sample is a whole brain sample.

In one embodiment, the acrolein solution is a 4%-10% acrolein solution.

In one embodiment, the Golgi-Cox solution comprises a 5% aqueous potassium dichromate solution, a 5% aqueous mercury chloride solution, a 5% aqueous potassium chromate solution and water in a volumetric ratio of 5:5:4:10, respectively.

In one embodiment, the Petropoxy 154 resin is composed of 90% of Petropoxy 154 resin and 10% of 99.5% ethanol.

In one embodiment, the Golgi-Cox solution is replaced twice in the step of replacing the Golgi-Cox solution.

In one embodiment, the Golgi-Cox solution is replaced at day 3 and day 7 in the step of replacing the Golgi-Cox solution.

In one embodiment, the neural tissue sample is gradiently dehydrated by alcohol in the step of gradiently dehydrating the neural tissue sample.

In one embodiment, the neural tissue sample is gradiently dehydrated by a 50%, 75%, 95%, and 100% alcohol solution in the step of gradiently dehydrating the neural tissue sample.

In one embodiment, before performing the step of gradiently dehydrating the neural tissue sample, the method further comprises the step of sectioning the neural tissue sample after the neural tissue sample is undergone being placed in the Golgi-Cox solution.

In one embodiment, between performing the step of sectioning the neural tissue sample after the neural tissue sample is undergone being placed in the Golgi-Cox solution and the step of gradiently dehydrating the neural tissue sample, the method further comprises the step of washing the neural tissue sample in water.

In one embodiment, between performing the step of incubating the neural tissue sample placed in the replaced Golgi-Cox solution at a temperature ranging from 36° C. to 38° C. and the step of sectioning the neural tissue sample after the neural tissue sample is undergone being placed in the Golgi-Cox solution, the method further comprises the step of washing the neural tissue sample in water.

In one embodiment, in the step of washing the neural tissue sample in water, the neural tissue sample is washed in water for one day.

In one embodiment, before performing the step of placing the fixed neural tissue sample in a Golgi-Cox solution in the dark, the method further comprises the step of washing the fixed neural tissue sample in water in the dark.

In one embodiment, in the step of washing the fixed neural tissue sample in water in the dark, the fixed neural tissue sample is washed in water for three days in the dark.

In one embodiment, in the step of embedding the dehydrated neural tissue sample with Petropoxy 154 resin, the dehydrated neural tissue sample is embedded with Petropoxy 154 resin at 70° C. overnight.

In one embodiment, in the step of placing a neural tissue sample in an acrolein solution in the dark for fixation, the neural tissue sample is fixed in the acrolein solution for overnight at 4° C.

In one embodiment, in the step of incubating the neural tissue sample placed in the replaced Golgi-Cox solution at a temperature ranging from 36° C. to 38° C., the neural tissue sample is placed in the replaced Golgi-Cox solution for seven days.

Accordingly, the method and kit for staining a neural tissue sample use the acrolein solution for fixation, use the Golgi-Cox solution for sample staining and thermal staining, and use Petropoxy 154 resin for embedding the dehydrated neural tissue sample, and have an elevated hit rate but without long-term staining. The method and kit may also be used with high-resolution X-ray microscopy to observe the detailed morphology and the neuroanatomical connectivity of the neural tissue sample.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The embodiments of the invention will be apparent from the following detailed description, which proceeds with reference to the accompanying drawings, wherein the same references relate to the same elements.

Figure 2A:
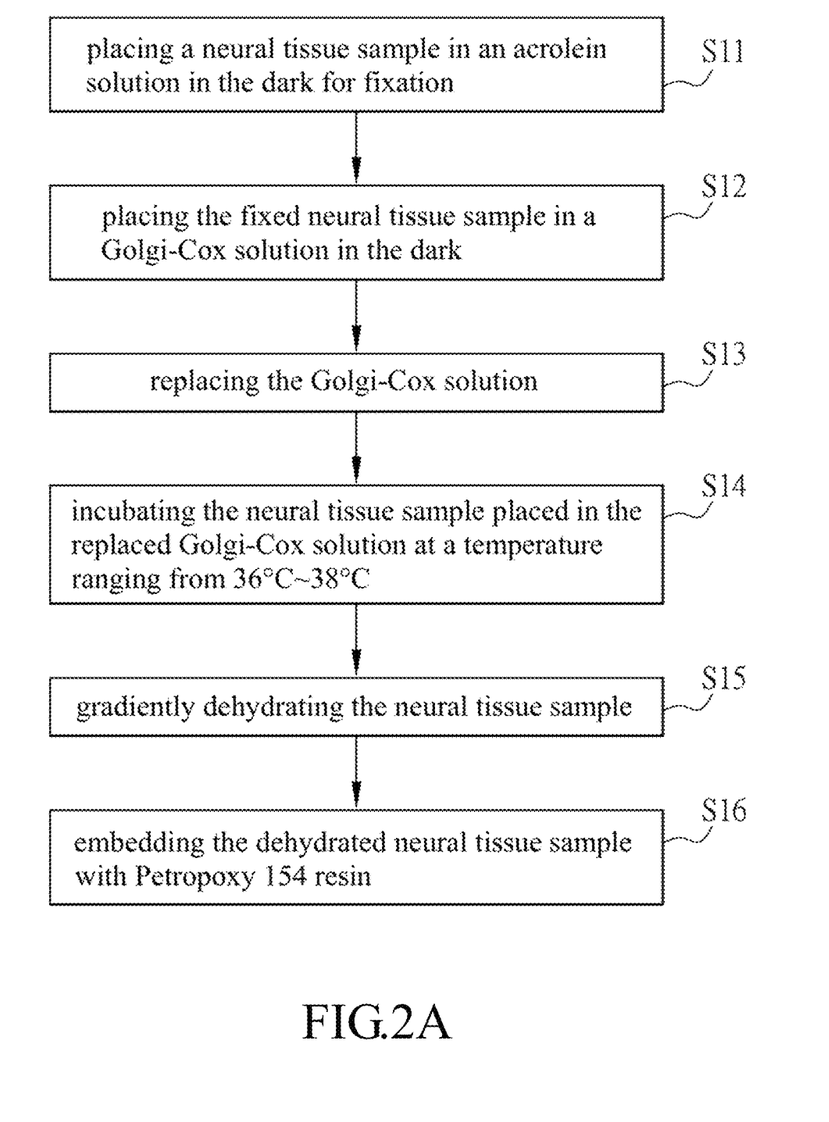
FIG. 2A is a flow chart of a method for staining a neural tissue sample according to one embodiment of the present disclosure.

FIG. 2A is a flow chart of a method for staining a neural tissue sample according to one embodiment of the present disclosure. As shown in FIG. 2A, the method or staining a neural tissue sample comprises the following steps: placing a neural tissue sample in an acrolein solution in the dark for fixation (step S11); placing the fixed neural tissue sample in a Golgi-Cox solution in the dark (step S12); replacing the Golgi-Cox solution (step S13); incubating the neural tissue sample placed in the replaced Golgi-Cox solution at a temperature ranging from 36° C. to 38° C. (step S14); gradiently dehydrating the neural tissue sample (step S15); and embedding the dehydrated neural tissue sample with Petropoxy 154 resin (step S16).

In the present embodiment, the neural tissue sample can be a whole brain sample obtained from a mouse. The obtained neural tissue sample is placed in the acrolein solution for tissue fixation, such that the original cellular and tissue morphology and structure of the neural tissue sample can be maintained as much as possible. The acrolein solution can be diluted in the PBS (phosphate buffered saline) buffer, and is preferable a 4% to 10% (v/v) acrolein solution diluted in the PBS buffer.

After fixation, the fixed neural tissue sample is placed in the Golgi-Cox solution in the dark (step S12). In the present embodiment, the neural tissue sample is placed in the Golgi-Cox solution at room temperature in the dark, and the Golgi-Cox solution comprises a 5% (w/v) aqueous potassium dichromate solution, a 5% (w/v) aqueous mercury chloride solution, a 5% (w/v) aqueous potassium chromate solution and water in a volumetric ratio of 5:5:4:10, respectively.

Later, the Golgi-Cox solution is replaced (step S13). The replacement of the Golgi-Cox solution means to replace the used solution with a fresh Golgi-Cox solution. The replacing times (i.e., how many times the solution are replaced) and the replacing interval are not limited herein. In the present embodiment, the Golgi-Cox solution can be replaced twice. The first replacement is to replace the Golgi-Cox solution used in the step S12 with a fresh Golgi-Cox solution, two days after the fixed neural tissue sample is placed in the Golgi-Cox solution in the dark. And, the second replacement is to replace the Golgi-Cox solution used in the first replacement with another fresh Golgi-Cox solution, five days after the first replacement.

After replacing the Golgi-Cox solution, the neural tissue sample placed in the replaced Golgi-Cox solution is incubated at a temperature ranging from 36° C. to 38° C. (step S14), which is a step of thermal staining. In the present embodiment, the neural tissue sample placed in the Golgi-Cox solution is incubated in an incubator at 37° C.

Later, the neural tissue sample is gradiently dehydrated (step S15). The gradient dehydration can be carried out with alcohol solutions serially diluted to various concentrations.

In details, the neural tissue sample is sequentially placed into the alcohol solutions with different concentrations, from low to high, to prevent the neural tissue sample from deformation resulted from acute dehydration. In the present embodiment, the neural tissue sample can be gradiently dehydrated with 50% (v/v), 75% (v/v), 95% (v/v), and 100% (v/v) aqueous alcohol solutions.

After the neural tissue sample is gradiently dehydrated, it can be embedded in Petropoxy 154 resin (step S16). In this step, the Petropoxy 154 resin is used for coloring and embedding. In the present embodiment, the gradiently dehydrated whole mouse brain (i.e. the neural tissue sample) which is fixed by the acrolein solution and stained and thermally stained by the Golgi-Cox solution can be embedded and colored with the Petropoxy 154 resin. For example, the Petropoxy 154 resin can be 100% Petropoxy 154 resin, and preferably 90% (v/v) Petropoxy 154 resin which is composed of 90% of Petropoxy 154 resin and 10% of 99.5% pure ethanol. Such concentration may facilitate the Petropoxy 154 resin to infiltrate into the tissue.

Figure 2B:
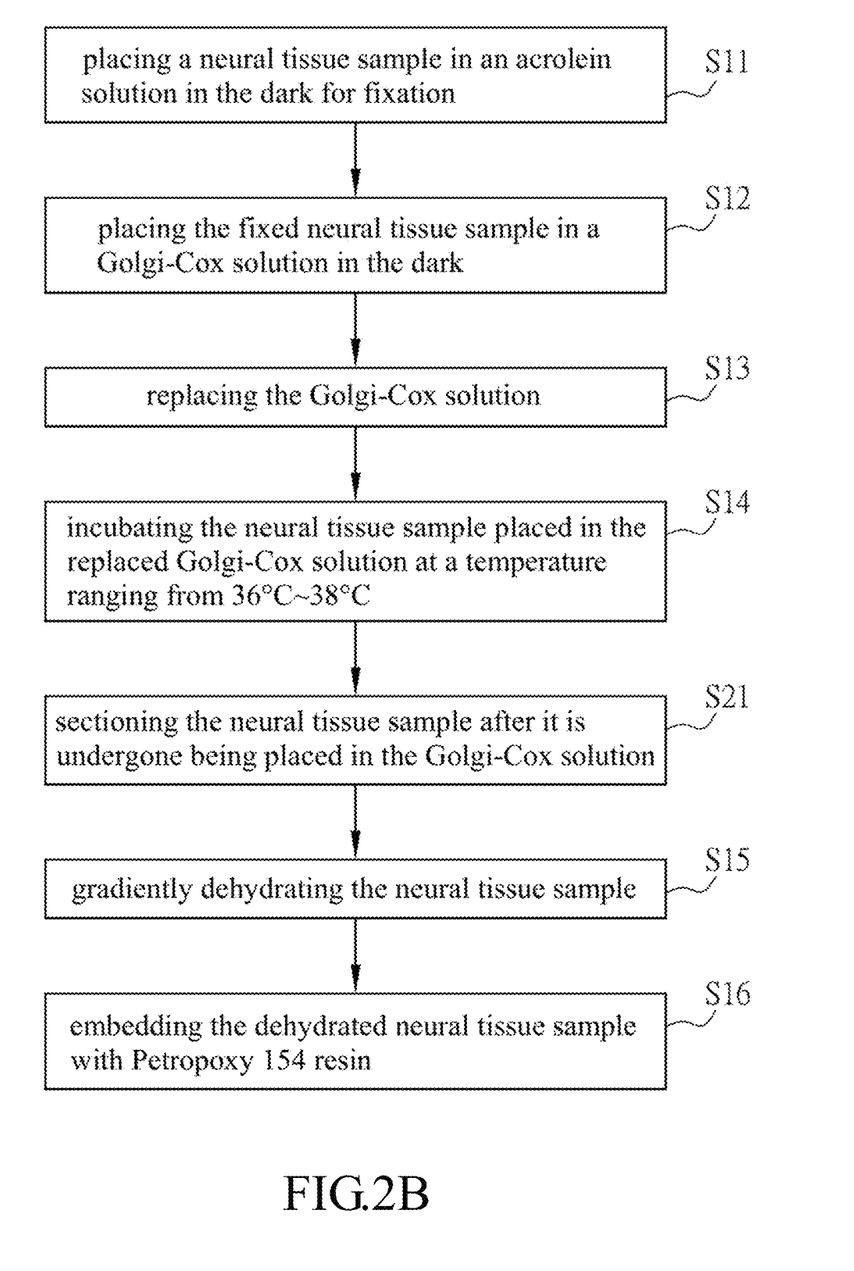
FIG. 2B is a flow chart of a method for staining a neural tissue sample according to another embodiment of the present disclosure.

FIG. 2B is a flow chart of another method for staining a neural tissue sample according to one embodiment of the present disclosure. As shown in FIG. 2B, the steps S11 to S16 is substantially the same as those counterparts in the previous embodiment and the details are omitted here. What is different between the flows of FIGS. 2A and 2B is that, in FIG. 2B, it is to perform the step S21 before the neural tissue sample is gradiently dehydrated. The step S21 is to section the neural tissue sample after it is undergone being placed in the Golgi-Cox solution. In details, after the neural tissue sample has been placed in the Golgi-Cox solution and undergone thermally staining, it can be sectioned firstly, followed by being gradiently dehydrated. The thickness of the sections of the neural tissue sample may vary with actual needs and range from dozens of micrometers to several millimeters, which is not limited here. In the present embodiment, after being fixed by the acrolein solution, stained and thermally stained with the Golgi-Cox solution, the whole mouse brain (i.e. the neural tissue sample) can be sectioned, followed by being graiently dehydrated and then colored and embedded with Petropoxy 154 resin.

Figure 3A:
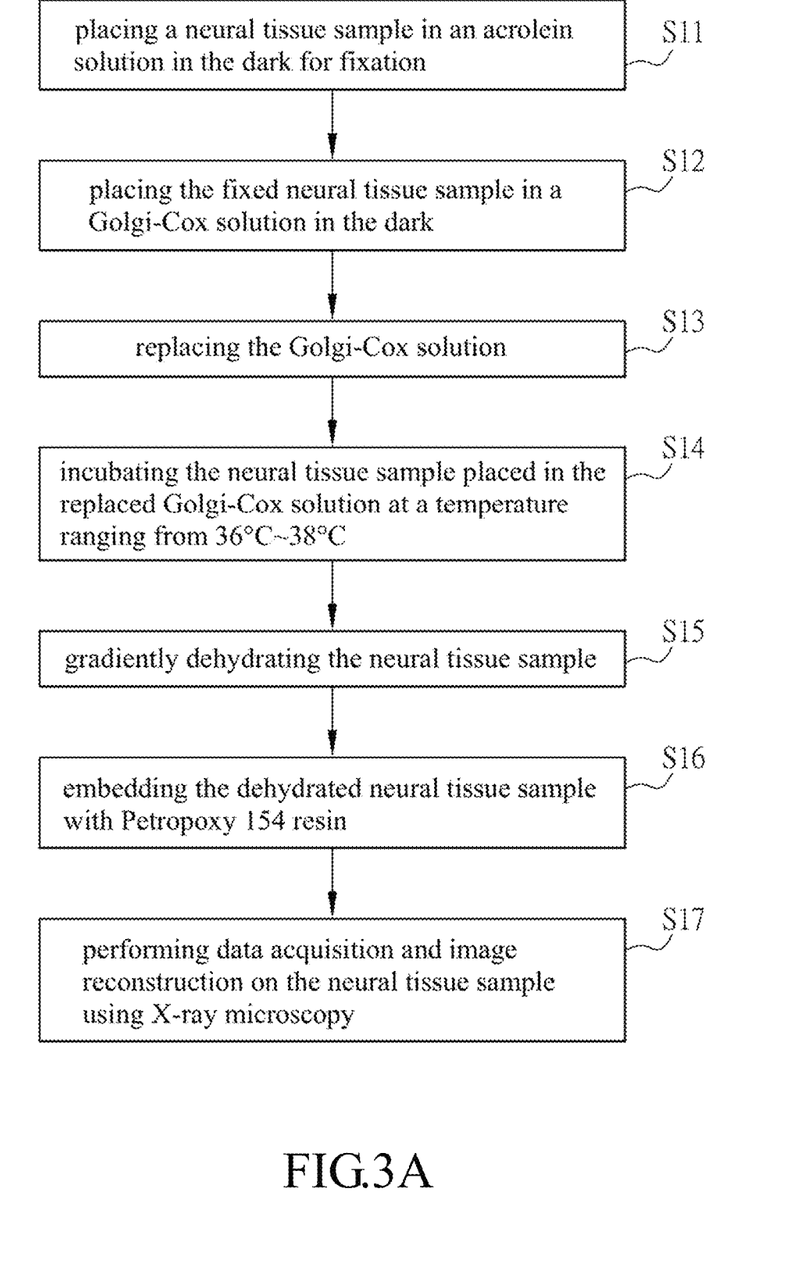
FIG. 3A is a flow chart of a method for visualizing neurons according to one embodiment of the present disclosure.
Figure 3B:
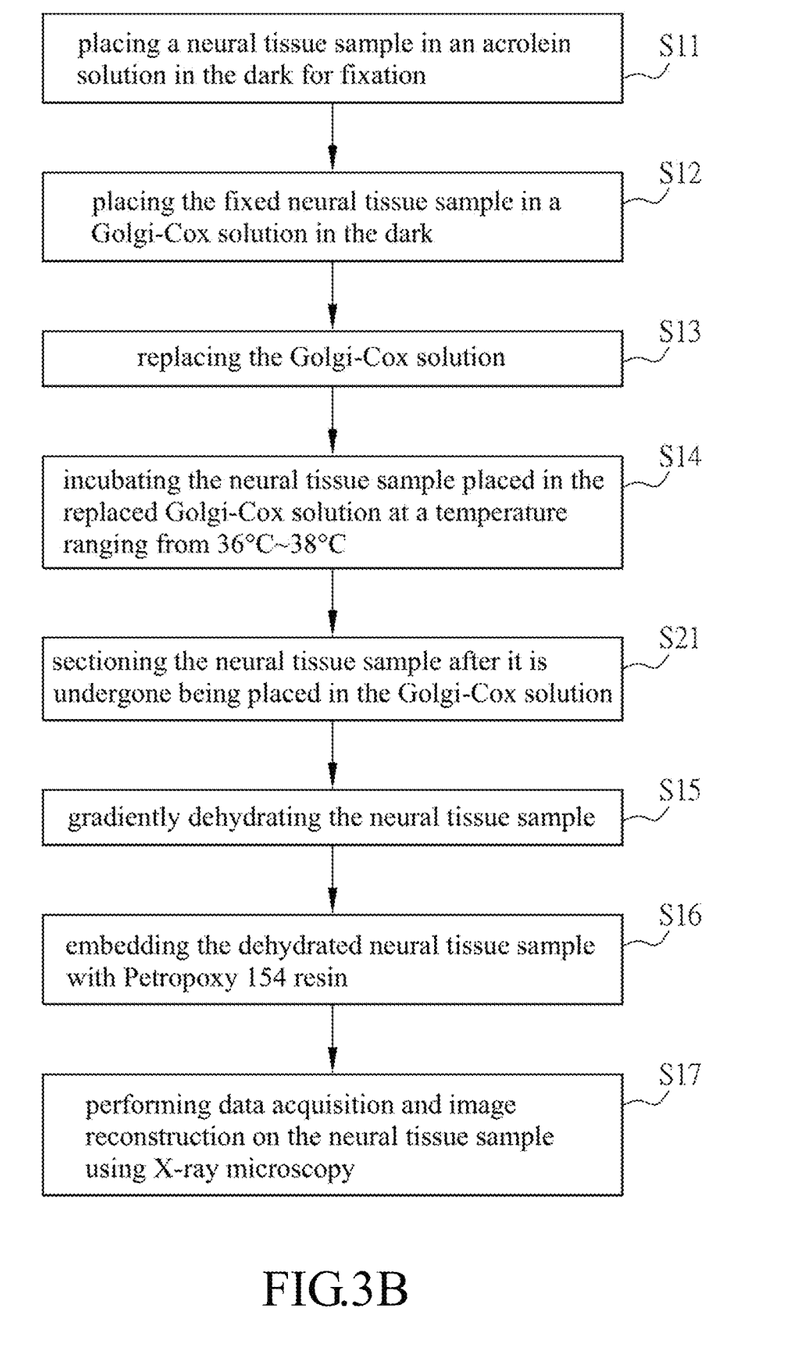
FIG. 3B is a flow chart of another method for visualizing neurons according to one embodiment of the present disclosure.

FIG. 3A is a flow chart of a method for visualizing neurons according to one embodiment of the present disclosure. FIG. 3B is a flow chart of another method for visualizing neurons according to one embodiment of the present disclosure. As shown in FIGS. 3A and 3B, it is to use the method(s) for staining the neural tissue sample as described in the preceding embodiments with the X-ray chromatography so as to collect image data of the neural tissue sample and to reconstruct the image thereof. Accordingly, the neurons and the neuroanatomical connectivity of the neural tissue sample can be revealed. In one embodiment, the neural tissue sample (such as the whole mouse brain) can be fixed by the acrolein solution, stained and thermally stained with the Golgi-Cox solution, followed by being gradiently dehydrated and then colored and embedded with Petropoxy 154 resin. The embedded neural tissue sample can be performed with the step of data acquisition and image reconstruction by a microscope system (refer to the step of S17 which recite "performing data acquisition and image reconstruction on the neural tissue sample using X-ray microscopy" in FIGS. 3A and 3B). Because the hit rate of the staining method provided by this disclosure can be raised to 25% to 35%, in the reconstructed image, both the neurons and the neuroanatomical connectivity can be observed. In addition, the method shown in FIG. 3A is applicable for reconstructing a large volumetric and high-resolution (of micron-scales) neuroanatomical image of a whole brain sample with X-ray tomography. The method exemplified in FIG. 3B is applicable for reconstructing a large volumetric and ultrahigh-resolution (of nano-scales) image of a tissue section with transmission X-ray microscopy (TXM). However, the present invention is not limited herein.

The present disclosure further provides a reagent kit for staining a neural tissue sample. The reagent kit comprises an acrolein solution, a Golgi-Cox solution and Petropoxy 154 resin. In one embodiment, the acrolein solution can be diluted to 4% (v/v) to 10% (v/v) with a PBS buffer. The Golgi-Cox solution can comprises a 5% (w/v) aqueous potassium dichromate solution, a 5% (w/v) aqueous mercury chloride solution, a 5% (w/v) aqueous potassium chromate solution and water, in a volumetric ratio of 5:5:4:10, respectively. In addition, the reagent kit for staining the neural tissue sample may further comprises a solution for gradiently dehydrating the neural tissue sample, such as an alcohol solution. In the present disclosure, the category of the reagent for gradiently dehydration is not limited, and the category of such reagent can comprises a variety of solutions which can gradiently dehydrate the tissue sample. Such reagent can be the solutions of the same type and with serially increased concentrations. In one embodiment, the solution for gradiently dehydrating the neural tissue sample can be the alcohol solutions with concentrations of 50% (v/v), 75% (v/v), 95% (v/v) and 100%.

In summary, the method and kit for staining a neural tissue sample utilize the acrolein solution for fixation, utilize the Golgi-Cox solution for sample staining and thermal staining, and use Petropoxy 154 resin for embedding the dehydrated neural tissue sample, and have an increased hit rate but without long-term staining. The method and kit may also be used with high-resolution X-ray microscopy to observe the detailed morphology and the neuroanatomical connectivity of the neural tissue sample.

In the following experimental examples, the practicing steps and functions of the method and kit for staining the neural tissue sample and the method for visualizing neurons are shown. It should be noted that the following examples are used to describe some practicing details so as to enable those skilled in the art to perform and/or use the method and kit disclosed by this disclosure, and they are not used to limit the scope of the present invention.

Example 1: Preparation of Golgi-Cox Solution

A Golgi-Cox solution comprised a 5% (w/v) aqueous potassium dichromate solution, a 5% (w/v) aqueous mercury chloride solution, a 5% (w/v) aqueous potassium chromate solution and water in a volumetric ratio of 5:5:4:10, respectively. Firstly, it was to prepare a solution A, solution B and solution C. The solution A was a 5% (w/v) aqueous potassium dichromate solution, prepared by dissolving 10 g of potassium dichromate in 200 ml of distilled water. The solution B was a 5% (w/v) aqueous mercury chloride solution, prepared by dissolving 10 g of mercury chloride in 200 ml of distilled water. The solution C was a 5% (w/v) aqueous potassium chromate solution, prepared by 8 g of potassium chromate in 160 ml of distilled water. The solutions A and B were mixed with each other in a 500 ml glass flask, and the solution C was mixed with 400 ml of distilled water in a 1000 ml glass flask. The mixed solution of A and B was slowly poured into the mixed solution of C and water and stirred with a glass rod simultaneously during pouring. After standing in the dark for 5 days, the supernatant of the resultant mixture was used for the following steps by aspiration (avoiding sediments).

Example 2: Preparation of Neural Tissue Samples

In the present experimental example, it was to obtain and then fix neural tissue samples. The C57BL/6J mice were used in this experimental example and deeply anesthetized with sodium pentobarbital (100 mg/Kg). The brain of each mouse was removed and immersed in the 10% acrolein solution (diluted in PBS buffer) and stand for overnight at 4° C. Later, the mouse brain was washed in water for three days in the dark.

Experiment 3: Staining of the Neural Tissue Sample

The neural tissue sample was stained and thermally stained with Golgi-Cox solution. The mouse brain was immersed in Golgi-Cox solution at room temperature and in the dark. Two days later, the Golgi-Cox solution was refreshed. On the fifth day after being immersed in the refreshed Golgi-Cox solution, the sample was replaced with another fresh Golgi-Cox solution, followed by being placed into a 37° C. incubator for thermally staining for seven days. Later, the mouse brain was washed in water for one day: the water was refreshed every three hours, and after the water was refreshed twice, the mouse brain was immersed in a fresh water and stand for overnight. The washed mouse brain can be used for coloring and embedding.

Example 4: Coloring and Embedding of the Neural Tissue Sample

The neural tissue sample prepared by the Example 3 was colored and embedded with Petropoxy 154 resin. The sample can be colored and embedded after section, or the whole brain sample can be directly colored and embedded. In this experimental example, the mouse brain sample can be sectioned at a thickness of 1 mm for X-ray micro-CT imaging, or 100 micrometers for X-ray nano-CT imaging. The sections were washed with water thrice (each time for five minutes) and dehydrated through a graded series of alcohol solutions with ascending concentrations (placed in 50% (v/v) ethanol once, and then 75% (v/v) ethanol once, 95% (v/v) ethanol once, last in 100% ethanol twice). After dehydration, the sections were embedded with Petropoxy 154 resin (containing 90% Petropoxy 154 resin and 10% of 99.5% ethanol) at 70° C. overnight for curing. Example 5: Coloring and Embedding with the conventional Golgi-Cox method The mouse brain sample was removed according to the steps described in the Example 2 and then immersed in the formaldehyde solution for fixation. The fixed mouse brain sample was stained with Golgi-Cox solutions according to the steps described in the Example 3. In this example, the mouse brain sample was colored with lithium hydroxide (LiOH) or ammonium hydroxide ($NH_4OH$) instead. The stained mouse brain was sectioned at a thickness of 100 micrometers. The sections were immersed in 1% (w/v) LiOH (or in 10% w/v $NH_4OH$) until the color of the samples was become black. It took about several minutes. The sections were then washed with water thrice (each time for five minutes) and dehydrated through a graded series of alcohol solutions with ascending concentrations (placed in 50% (v/v) ethanol once, and then 75% (v/v) ethanol once, 95% (v/v) ethanol once, last in 100% ethanol twice). At last, the sections were embedded in Epon 812 resin.

Example 6: Data Acquisition and Image Reconstruction

The reconstructed image of a large volumetric and high-resolution (of micro-scales) was taken with X-ray tomography by using the BL01A beamline from the storage ring of the NSRRC (Taiwan National Synchrotron Radiation Research Center). The aforementioned beamline was a full-spectrum X-ray beamline. The X-ray was passed through an attenuator to reduce its intensity. After that, the X-ray was then passed through the sample and then converted to a visible light by a scintillation crystal. The visible light was then introduced into an objective and detectors through prisms.

The specimen was mount on the sample carrier. Each sample was imaged with an exposure time of 200 milliseconds (ms) on every 0.3°. After taking 600 images consecutively, those images were reconstructed by Octopus Imaging Software. The 3D image was produced by Amira software (AMIRA®).

The reconstructed image of a large volumetric and high-resolution (of nano-scales) was taken with transmission X-ray microscopy by using the BL01B beamline from the storage ring of the NSRRC (Taiwan National Synchrotron Radiation Research Center). The aforementioned beamline was an X-ray beamline with a certain wavelength. The X-ray was passed through an X-ray tube to focus. After that, the focused X-ray was then passed through a pinhole and then focused on the sample. The light which was passed through the sample was passed through a Fresnel waveband to magnify the image and then passed through a phase ring to generate a phase difference. At last, the X-ray was converted to a visible light by a scintillation crystal, magnified again by the objective, and imaged by a detector. The energy of the imaging X-ray was 8 KeV and each image was taken with an exposure time of 50 ms.

Figure 4:
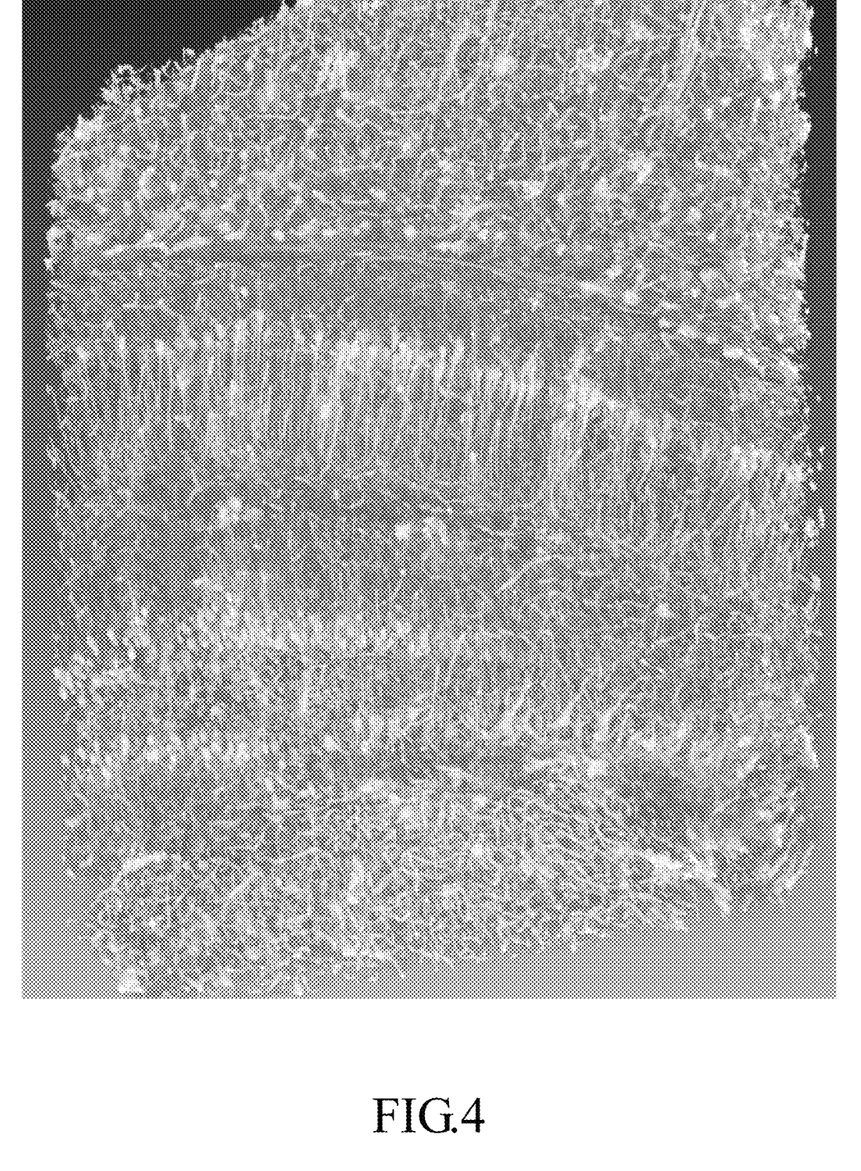
FIG. 4 is an image of a large volumetric and high-resolution (in a micron-scale) reconstruction of a mouse hippocampus acquired through the staining method according to one embodiment of the present disclosure.

FIG. 4 is an image of a large volumetric and high-resolution (in a micron-scale) reconstruction of a mouse hippocampus of a whole mouse brain sample acquired through the preparing and staining processes of Examples 1 to 3 and embedding process of Example 4 with Petropoxy 154 resin. The image was taken according to the aforementioned procedures. The size of the mouse hippocampus sample was 383×1376×1835 (thickness×width×height) micrometers, and the image was taken with the X-ray tomography by using the BL01A beamline with a 5× objective. From FIG. 4, the hit rate of the method for staining neurons with Golgi-Cox solution provided by the embodiments of the present disclosure was significantly increased. When comparing with the conventional Golgi-Cox staining methods, the method provided by the present disclosure can increase the hit rate for a dozen folds to about 25% to 30%.

Figure 5:
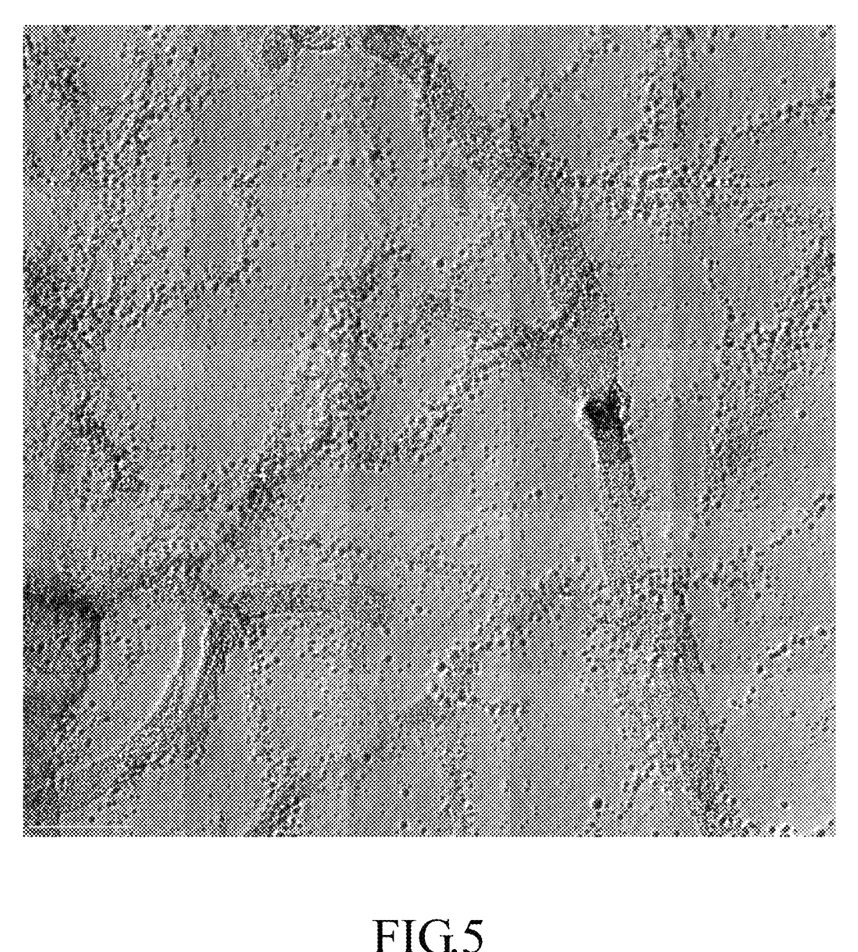
FIG. 5 is an ultra-high resolution (in a nano-scale) microscopic image of neurons stained by a conventional Golgi-Cox staining method.
Figure 6:
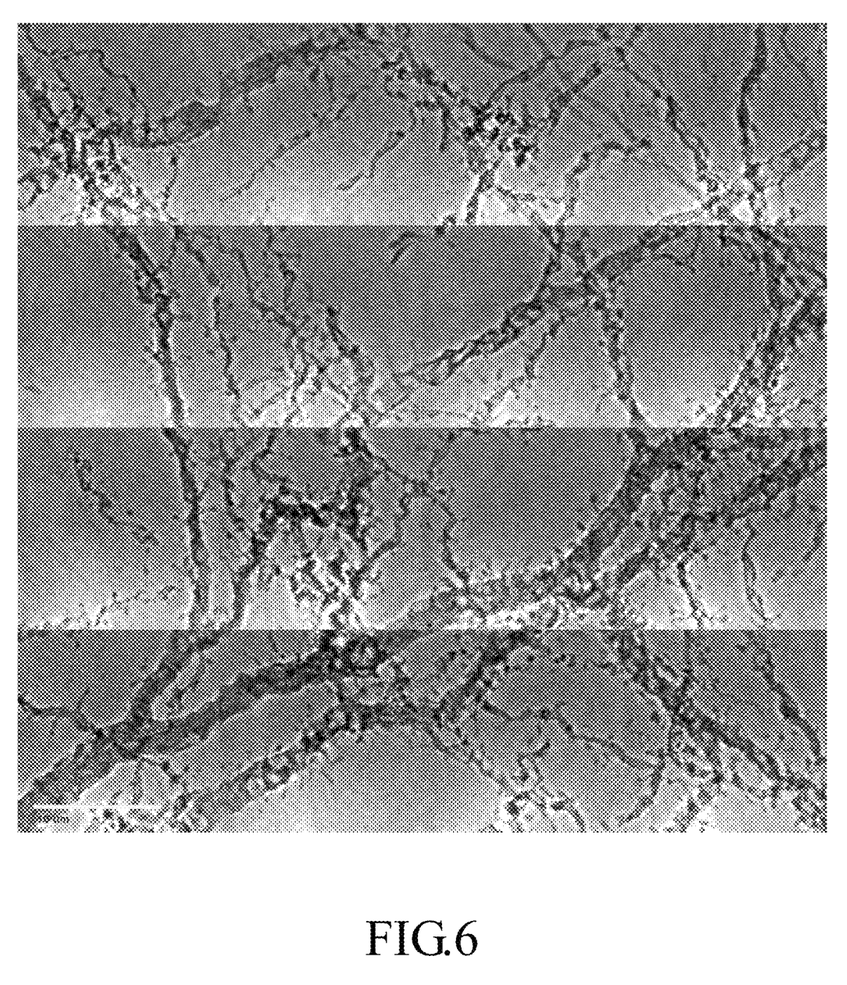
FIG. 6 is an ultra-high resolution (in a nano-scale) microscopic image of neurons stained by the staining method according to one embodiment of the present disclosure.

Please refer to FIGS. 5 and 6. FIG. 5 is an ultra-high resolution (in nano-scales) microscopic image of neurons stained by a conventional Golgi-Cox staining method, colored with LiOH/$NH_4OH$. FIG. 6 is an ultra-high resolution (in nano-scales) microscopic image of neurons prepared and stained through the processes of Examples 1 to 3 and embedded through the process of Example 4 with Petropoxy 154 resin. In detail, the neural tissue sample was stained by the conventional Golgi-Cox staining process and colored with LiOH/$NH_4OH$ (as described in Example 5). The neural tissue sample was stained through the steps of the method provided by the present disclosure. The images of both neural tissue samples were taken with a high-resolution transmission X-ray microscopy (TXM, resolution of 40 nanometers) to acquire data and reconstruct the image. It could be found that, even both were taken under the same high-resolution X-ray microscopy, many granular structures could be observed in FIG. 5, which makes it is difficult to determine whether the locations of granules aggregations were just background noises or actually the dendrites or axons of neurons, not to mention to observe the connectivity of neurons. On the contrary, the image of the dendrites and axons of neurons were shown to be continuous patterns in FIG. 6. In other words, the dendrites and axons could be clearly observed in the reconstructed image, which can be used to observe the connectivity of the neurons.

The experimental results clearly demonstrate that the method and kit for staining the neural tissue sample and method for visualizing neurons can significantly increase the hit rate of staining neurons, and the dendrites/axons of neurons can be shown in a continuous pattern in the high-resolution reconstructed image. Hence, the connectivity of neurons can be clearly shown through processing the neural tissue sample by the method and kit provided by the present disclosure. As described above, the method and kit for staining a neural tissue sample provided by this disclosure use the acrolein solution for fixation, use the Golgi-Cox solution for sample staining and thermal staining, and use Petropoxy 154 resin for embedding the dehydrated neural tissue sample, and have an increased hit rate but without long-term staining. The method and kit may also be used with high-resolution X-ray microscopy to observe the detailed morphology and the neuroanatomical connectivity of the neural tissue sample.

Although the present invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the present invention.

What is claimed is:

1. A method for visualizing neurons, comprising:
a staining step, comprising:
placing a neural tissue sample in an acrolein solution in the dark for fixation;
placing the fixed neural tissue sample in a Golgi-Cox solution in the dark;
replacing the Golgi-Cox solution;
incubating the neural tissue sample placed in the replaced Golgi-Cox solution at a temperature ranging from 36° C. to 38° C.;
gradiently dehydrating the neural tissue sample;
embedding the dehydrated neural tissue sample with Petropoxy 154 resin, wherein the Petropoxy 154 resin is composed of 90% of Petropoxy 154 resin and 10% of 99.5% ethanol; and
a visualizing step, comprising:
visualizing and image-taking the neural tissue sample using X-ray microscopy.

2. The method according to claim 1, wherein the neural tissue sample is a whole brain sample.

3. The method according to claim 1, wherein the acrolein solution is a 4%-10% (v/v) acrolein solution.

4. The method according to claim 1, wherein the Golgi-Cox solution comprises a 5% aqueous potassium dichromate solution, a 5% aqueous mercury chloride solution, a 5% aqueous potassium chromate solution and water in a volumetric ratio of 5:5:4:10, respectively.

5. The method according to claim 1, wherein the Golgi-Cox solution is replaced twice in the step of replacing the Golgi-Cox solution.

6. The method according to claim 5, wherein the Golgi-Cox solution is replaced at day 3 and day 7 in the step of replacing the Golgi-Cox solution after placing the fixed neural tissue sample in a Golgi-Cox solution in the dark.

7. The method according to claim 1, wherein the neural tissue sample is gradiently dehydrated by alcohol in the step of gradiently dehydrating the neural tissue sample.

8. The method according to claim 7, wherein the neural tissue sample is gradiently dehydrated by a 50%, 75%, 95%, and 100% alcohol solution in the step of gradiently dehydrating the neural tissue sample.

9. The method according to claim 1, before performing the step of gradiently dehydrating the neural tissue sample, further comprising:
sectioning the neural tissue sample after the neural tissue sample is undergone being placed in the Golgi-Cox solution.

10. The method according to claim 9, between performing the step of sectioning the neural tissue sample after the neural tissue sample is undergone being placed in the Golgi-Cox solution and the step of gradiently dehydrating the neural tissue sample, further comprising:
washing the neural tissue sample in water.

11. The method according to claim 9, between performing the step of incubating the neural tissue sample placed in the replaced Golgi-Cox solution at a temperature ranging from 36° C. to 38° C. and the step of sectioning the neural tissue sample after the neural tissue sample is undergone being placed in the Golgi-Cox solution, further comprising:
washing the neural tissue sample in water.

12. The method according to claim 11, wherein in the step of washing the neural tissue sample in water, the neural tissue sample is washed in water for one day.

13. The method according to claim 1, before performing the step of placing the fixed neural tissue sample in a Golgi-Cox solution in the dark, further comprising:
washing the fixed neural tissue sample in water in the dark.

14. The method according to claim 13, wherein in the step of washing the fixed neural tissue sample in water in the dark, the fixed neural tissue sample is washed in water for three days in the dark.

15. The method according to claim 1, wherein in the step of embedding the dehydrated neural tissue sample with Petropoxy 154 resin, the dehydrated neural tissue sample is embedded with Petropoxy 154 resin overnight at 70° C.

16. The method according to claim 1, wherein in the step of placing a neural tissue sample in an acrolein solution in the dark for fixation, the neural tissue sample is fixed in the acrolein solution for overnight at 4° C.

17. The method according to claim 1, wherein in the step of incubating the neural tissue sample placed in the replaced Golgi-Cox solution at a temperature ranging from 36° C. to 38° C., the neural tissue sample is placed in the replaced Golgi-Cox solution for seven days.

* * * * *